United States Patent
Hwang et al.

(10) Patent No.: US 10,253,012 B2
(45) Date of Patent: Apr. 9, 2019

(54) METHOD AND APPARATUS FOR PREPARATION OF LACTIDE USING LACTIDE PURIFICATION PROCESS

(71) Applicant: KOREA RESEARCH INSTITUTE OF CHEMICAL TECHNOLOGY, Daejeon (KR)

(72) Inventors: Dong Won Hwang, Daejeon (KR); Jong San Chang, Daejeon (KR); Young Kyu Hwang, Daejeon (KR); U Hwang Lee, Daejeon (KR); Do Young Hong, Gyeonggi-do (KR); Su Kyung Lee, Daejeon (KR); Kyung Ho Cho, Gyeonggi-do (KR); Pravin Pandharinath Upare, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 15/290,647

(22) Filed: Oct. 11, 2016

(65) Prior Publication Data

US 2017/0101390 A1 Apr. 13, 2017

(30) Foreign Application Priority Data

Oct. 12, 2015 (KR) .................. 10-2015-0142330

(51) Int. Cl.
*C07D 319/12* (2006.01)
*B01D 9/00* (2006.01)
*B01D 39/00* (2006.01)

(52) U.S. Cl.
CPC ......... *C07D 319/12* (2013.01); *B01D 9/0009* (2013.01); *B01D 39/00* (2013.01); *C07B 2200/13* (2013.01)

(58) Field of Classification Search
CPC ... C07D 319/12; B01J 8/0278; B01J 2208/02; B01D 3/00; B01D 9/0009; B01D 39/00; C07B 2200/13
See application file for complete search history.

(56) References Cited

U.S. PATENT DOCUMENTS

| 4,835,293 | A | * | 5/1989 | Bhatia | B01J 19/1862 549/274 |
| 5,053,522 | A | * | 10/1991 | Muller | C07C 59/10 502/151 |
| 5,247,059 | A | | 9/1993 | Gruber et al. | 528/354 |
| 5,274,073 | A | | 12/1993 | Gruber et al. | 528/354 |
| 5,274,127 | A | | 12/1993 | Sinclair et al. | 549/274 |
| 5,332,839 | A | | 7/1994 | Benecke et al. | 549/274 |
| 5,502,215 | A | | 3/1996 | Yamaguchi et al. | 549/274 |
| 5,866,719 | A | * | 2/1999 | Desantis | C07C 213/10 564/497 |
| 6,277,951 | B1 | | 8/2001 | Gruber et al. | 528/354 |
| 9,221,938 | B2 | * | 12/2015 | Krull | B01J 19/126 |
| 2013/0267716 | A1 | * | 10/2013 | Hong | C07D 319/12 549/274 |
| 2015/0239863 | A1 | * | 8/2015 | Hwang | B01J 21/04 549/274 |

FOREIGN PATENT DOCUMENTS

| KR | 10-0261850 | | 8/2000 |
| KR | 10-2014-0024188 | * | 2/2014 |
| KR | 10-1376483 | | 2/2014 |

OTHER PUBLICATIONS

KR-10-2014-0024188 English machine translations K-PION, Google Translate, p. 1-45.*
ICSC 0554—Isopropyl Alcohol; http://www.ilo.org/dyn/icsc/showcard.display?p_card_id=0554[Apr. 19, 2017; p. 1.*
Armarego, W. L. F., "Purification of Laboratory Chemicals 2003." Reed Educational and Professional Publishing Ltd.*
Smith, R., Chemical process: design and integration. John Wiley & Sons, 2005.*
Chen, Z., "Determination and correlation of solubility data and dissolution thermodynamic data of L-lactide in different pure solvents." Journal of Chemical & Engineering Data 58.1 (2012): 143-150. (Year: 2012).*

* cited by examiner

*Primary Examiner* — John M Mauro
(74) *Attorney, Agent, or Firm* — Norton Rose Fulbright US LLP

(57) ABSTRACT

The present invention relates to a method and apparatus for preparation of lactide using a lactide purification process, comprising introducing an aqueous solution comprising lactic acid into a reactor filled with a catalyst and reacting the same to produce crude lactide vapor; and purifying the crude lactide vapor to produce lactide crystals, wherein a first purification comprises collecting and crystallizing the crude lactide vapor using a first solvent to produce lactide crystals, and separating the lactide crystal from a residue through filtration.

15 Claims, 1 Drawing Sheet

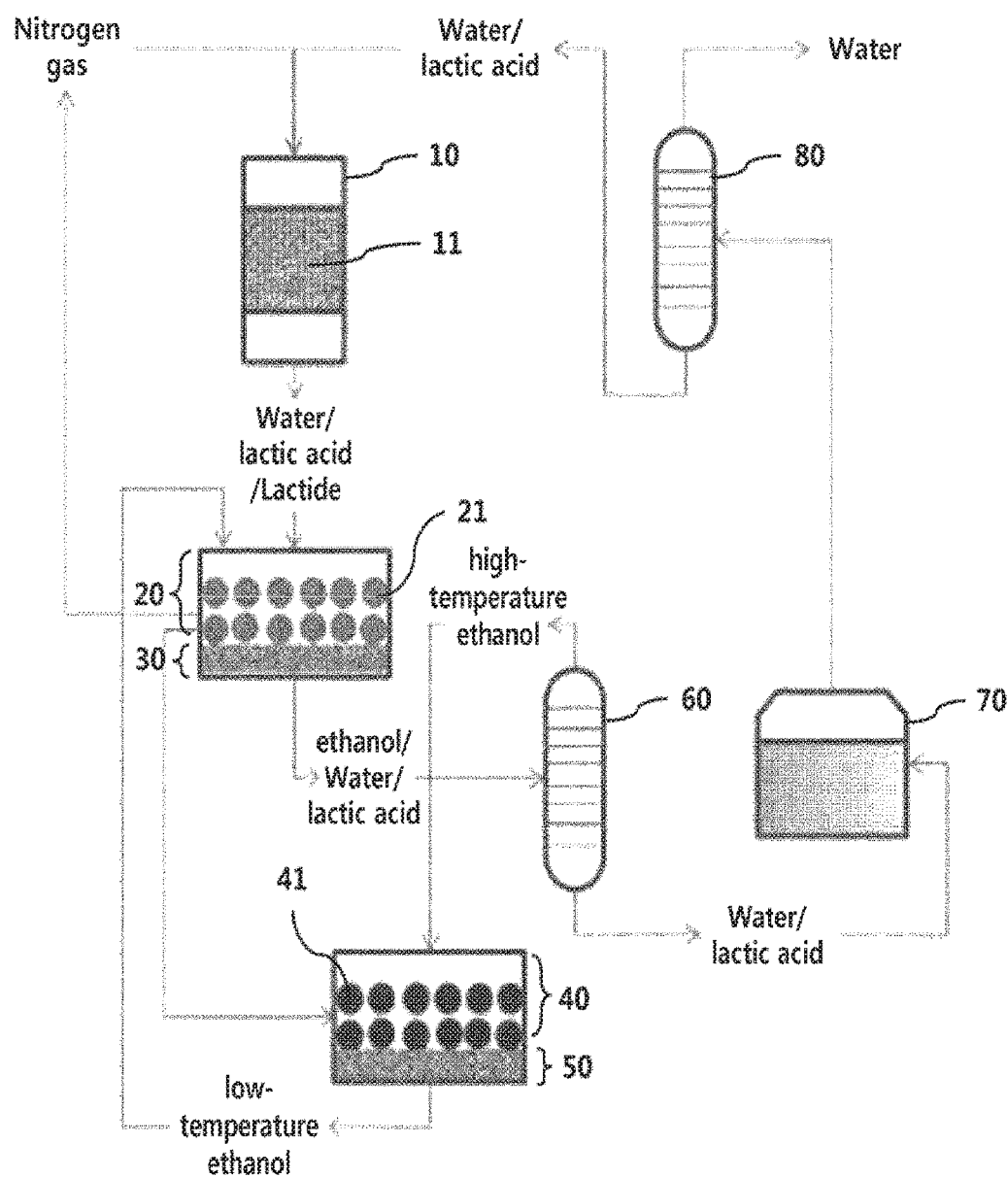

METHOD AND APPARATUS FOR PREPARATION OF LACTIDE USING LACTIDE PURIFICATION PROCESS

CROSS-REFERENCE TO RELATED APPLICATIONS

This application claims the benefit of Korean Patent Application No. 10-2015-0142330, filed Oct. 12, 2015. The contents of the referenced application are incorporated herein by reference.

TECHNICAL FIELD

The present invention relates to a method and apparatus for preparation of lactide using a lactide purification process, more specifically to a method and apparatus for preparation of lactide, in which lactide vapor is cooled rapidly using a solvent to prevent side reactions and lactide is crystallized and separated, in the process of collecting and purifying the lactide vapor produced by a direct preparation method for lactide from lactic acid.

BACKGROUND ART

Polylactic acid (PLA or polylactide) is a polymer having optical character, and is used in sutures for surgery, microcapsules for injection, and other biomedical materials for biodegradation, and is a biodegradable eco-friendly material which can be used in packing materials, electronic appliances, office supplies, vehicle interior materials, and various polymer products.

In order for the polylactic acid to be used for the above purposes, a high optical purity (D-type or L-type optical isomers) and a high molecular weight are required, which requires a high optical purity and a chemical purity of lactide, a monomer used in a preparation of polylactide.

A traditional method of preparing lactide from lactic acid goes through a two-step reaction of primarily polymerizing lactic acid under reduced pressure to obtain a prepolymer with a molecular weight of 500 to 5000, and depolymerizing the prepolymer under inactive gas flow and reduced pressure, thereby obtaining lactide, as shown in Route (1) of Reaction 1 (U.S. Pat. Nos. 5,274,073, 5,247,059, 5,274,127, and 6,277,951). Commercially, Nature Works in the U.S. has been producing lactide from L-type lactic acid raw material through the two-step reaction and polycondensation of the lactide in a polymerization reactor to produce about 140,000 tons of L-type PLA bioplastics annually. Also, Purac in the Netherlands has recently built factories for the preparation process of lactide by the two-step reaction in Thailand and initiated commercial production thereof.

However, using the two-step reaction may result in deterioration of the prepolymer and the lactide products in the reactor over a long period of time, causing a problem of increased production of a byproduct, meso-lactide, during production of L- or D-lactide. The two-step process of lactide production by prepolymerization-depolymerization has problems in that a prepolymer oligomer, which is a reactant in the depolymerization step, is not degraded into lactide, some oligomers are over-polymerized, and waste mixed with catalysts contained in the prepolymer is produced. Additionally, the two-step reaction process requires a vacuum pump for reducing high vacuum pressure, and the reaction apparatus is very complex and excessively costly.

Meanwhile, as another traditional method for preparing lactide from lactic acid, there exists a method which directly prepares lactide via a fixed bed reactor filled with solid acid catalysts by evaporating lactic acid at a temperature at 200° C. or higher without going through a prepolymer, as shown in Route (2) of Reaction 1 (U.S. Pat. No. 5,332,839). In particular, the present inventors suggested a direct preparation method of lactide using a nanocomposite catalyst comprising tin oxide as a main component to prepare lactide from an aqueous solution of lactic acid, and this method enables a stable production of lactide with a high yield of 90% or higher (Korean Patent No. 1376483).

[Reaction 1]

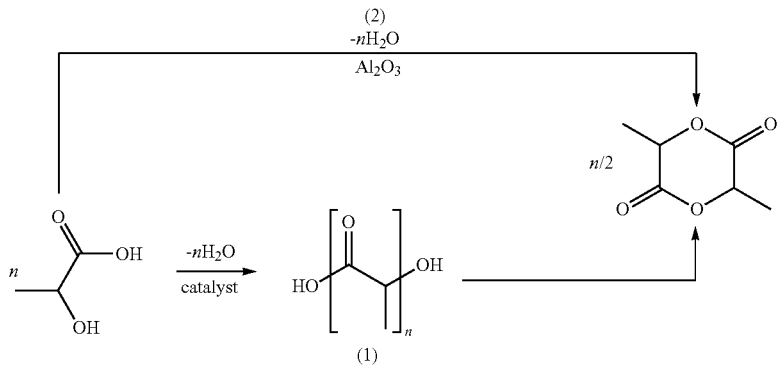

In the case of using a nanocomposite catalyst comprising tin oxide as a main component, the lactide produced after the catalytic reaction is present in the form of vapor along with water, unreacted lactic acid, and carrier gases, which are byproducts of the reaction. Meanwhile, as lactide readily reacts with water and lactic acid and denatures to a lactic acid dimer or trimer, the lactide which is produced after the catalytic reaction needs to be rapidly separated from water and lactic acid.

As one of purification and separation methods, a method of separating meso-lactide using the differences in the solubility in water and the rate of hydrolysis between the meso-lactide and D- and L-lactide has been extensively studied (Reference: U.S. Pat. No. 5,502,215). However, such method is disadvantageous in that the separation is not efficient as it is a technique of merely stirring lactide and water at room temperature. Additionally, the lactide is dissolved in a solvent immiscible with water to be in contact with water to eliminate components through extraction. However, such method does not sufficiently separate L- or D-lactide from meso-lactide.

In Korean Patent No. 10-0261850 (Title of Invention: Preparation method of polylactide using improved purification process, hereinafter referred to as Conventional Technology 1), as a preparation method for polylactide comprising providing a crude lactide mixture comprising at least one lactide selected from the group consisting of meso-, L-, and D-lactide, a preparation method for polylactide comprising distilling the crude lactide mixture without extracting solvent or recrystallizing to purify the mixture as at least one lactide fraction; and polymerizing the purified lactide fraction to form polylactide is disclosed.

PRIOR ART

Patent Document (Patent Document 1) Korean Patent No. 10-0261850 B1

DISCLOSURE OF INVENTION

Technical Problem

Conventional distillation technology for lactide purification has a first problem in that a thermal polymerization or hydrolysis of lactide occurs during distillation, leading to a decrease in lactide yield, and a second problem in that the apparatus for the distillation method is complicated, and not only the installation fee but also the energy expenditure is high.

A purpose of the present invention is to provide a method and apparatus for preparation of lactide, comprising rapidly cooling vapor using a solvent to prevent side reactions, and at the same time, crystallizing and separating the lactide in a lactide purification process.

However, the technical problems of the present invention should not be limited to those described above, and other technical problems not described above will be obvious to one of ordinary skill in the art from the description provided hereinbelow.

Technical Solution

A first aspect of the present invention is to provide a method for preparing lactide comprising introducing an aqueous solution comprising lactic acid into a reactor filled with a catalyst and reacting the same to produce crude lactide vapor; and purifying the crude lactide vapor to produce lactide crystals (first purification step), wherein the first purification comprises collecting and crystallizing the crude lactide vapor using a first solvent to produce lactide crystals, and separating the lactide crystals from the residue through filtration.

A second aspect of the present invention is to provide a lactide crystal produced according to the first aspect.

A third aspect of the present invention is to provide an apparatus for preparing lactide comprising a catalytic reaction unit (10) filled with a solid catalyst (11) into which an aqueous solution comprising lactic acid is introduced to produce lactide vapor; a condensing unit (20) filled with a first solvent into which the crude lactide vapor produced in the catalytic reaction unit (10) is introduced to collect and crystallize the crude lactide vapor, thereby producing lactide crystals (21); and a first filtration unit (30), into which the lactide crystals (21) produced in the condensing unit (20) and the residue are introduced to separate the lactide crystals (21) by filtration.

Preferably, the first solvent may be at least one selected from the group consisting of ethanol, propanol, and butanol.

Preferably, the first solvent may cool, collect, and crystallize the crude lactide vapor at a temperature between 5° C. and 20° C.

Preferably, the solubility of lactide in the first solvent may be 0.1 or less at a temperature between 5° C. and 20° C.

Preferably, the vapor pressure of the first solvent may be between 5 hPa and 70 hPa at 20° C.

Preferably, the steps (ii-a) and (ii-b) may be conducted simultaneously.

Preferably, the step of collecting and crystallizing the crude lactide vapor using the first solvent to produce lactide crystals and the step of separating the lactide crystals from the residue through filtration may be performed simultaneously.

Preferably, the method of the present invention may further comprise re-purifying the lactide crystals after the first purification step (second purification step); wherein the second purification comprises dissolving the lactide crystals in a second solvent which has the same components as the first solvent, recrystallizing the dissolved lactide crystals, and filtering and separating the recrystallized lactide crystals from the second solvent.

Preferably, the weight ratio between the second solvent in the dissolving step and the lactide crystals may be between 1:1 and 1:5.

Preferably, the dissolution temperature in the dissolving step may be between 40° C. and 80° C.

Preferably, in the recrystallization step, the lactide crystals may be cooled and recrystallized at a temperature between $-10°$ C. and 30° C.

Preferably, the method of the present invention may further comprise re-supplying the second solvent separated in the second purification step as the first solvent of the first purification step.

Preferably, the second purification step may be repeated at least once.

Preferably, the method of the present invention may further comprise distilling the residue separated in the first purification step to obtain the first solvent between the first and second purification steps and introducing the obtained first solvent as the second solvent of the second purification step.

Preferably, the catalyst a tin-containing solid catalyst comprising a tin(IV) oxide or a mixed or complex oxide thereof containing the oxidized state (IV) of tin.

Preferably, the solid catalyst may comprise an oxide of at least one metal selected from the group consisting of Si, Ti, Al, Zn, Zr, V, Cr, Mn, Fe, and Mo.

Additionally, the present invention provides a lactide crystal having an optical purity of 98% or higher which is produced according to first aspect.

Additionally, the present invention provides lactide crystals produced according to first aspect.

Additionally, the present invention provides an apparatus for preparing lactide comprising a catalytic reaction unit (10) filled with a solid catalyst(11) into which an aqueous solution of lactic acid is introduced to produce crude lactide vapor; a condensing unit (20) filled with a first solvent into which the crude lactide vapor produced in the catalytic reaction unit (10) is introduced to collect and crystallize the crude lactide vapor, thereby producing lactide crystals (21); and a first filtration unit (30), into which the lactide crystals

(21) produced in the condensing unit (20) and a residue are introduced to separate the lactide crystals (21) by filtration.

Preferably, the apparatus of the present invention may further comprise a first recrystallization unit (40), into which the lactide crystals (21) obtained by the first filtration unit (30) and the second solvent comprising the same components as the first solvent are introduced and in which the lactide crystals (21) are dissolved and recrystallized by the second solvent; and a second filtration unit (50), into which the recrystallized lactide crystals (41) and the second solvent are introduced to separate the recrystallized lactide crystals (41) by filtration.

Preferably, the apparatus of the present invention may further comprise a distillation unit (60), into which the residue separated by the first filtration unit (30) is introduced, which is then distilled to obtain the first solvent, wherein the distillation unit (60) supplies the first solvent obtained by the distillation unit (60) to the first recrystallization unit (40) as the second solvent.

Preferably, the second filtration unit (50) may further carry out a function of re-supplying the second solvent separated in the second filtration unit (50) to the condensing unit (20) as the first solvent.

Preferably, the apparatus of the present invention may further comprise a second recrystallization unit, which has the same function as the first recrystallization unit (40) and into which the recrystallized lactide crystals (41) separated in the second filtration unit (50) are introduced, and a third filtration unit.

Advantageous Effect

Compared to the conventional technology, the preparation method for lactide using the lactide purification process according to the present invention has a first advantage of minimizing loss of lactic acid and converting lactide vapor into lactide crystals, thereby increasing the production yield of lactide, a second advantage of simply filtering the lactide crystals from lactic acid and water and drying the same to recover pure lactide crystals, thereby reducing production cost with simplified production process, and a third advantage of completing the lactide preparation process directly from the aqueous solution of lactic acid by the present invention without going through the lactic acid prepolymer.

DESCRIPTION OF DRAWINGS

The provided FIGURE shows a schematic diagram of the apparatus for preparation of lactide according to an embodiment of the present invention.

BEST MODE

Hereinbelow, the present invention will be described with reference to the accompanying drawings. However, the present invention may be described in different forms and should not be construed as being limited to the descriptions set out herein. Additionally, some elements unrelated to the descriptions may be omitted in the drawings to aid in understanding the invention, and like reference numerals designate like elements throughout the specification.

As used herein, when a part is referred to as being "linked (connected, contacted, combined)" to another part, it can be "directly linked" to the other part or "indirectly linked" thereto via intervening parts. Additionally, when a part "includes" an element, unless contrarily defined, it can further include other elements rather than excluding the same.

The terminology used herein is for the purpose of describing particular embodiments only and is not intended to be limiting. As used herein, the singular forms "a", "an", and "the" are intended to include the plural forms as well, unless the context clearly indicates otherwise. It will be further understood that the terms "comprise", "include", "have", etc., when used in this specification, specify the presence of stated features, integers, steps, operations, elements, components, and/or combinations thereof but do not preclude the presence or addition of one or more other features, integers, steps, operations, elements, components, and/or combinations thereof.

In addition, it will be understood that when an element such as a layer, a film, a region, or a plate is referred to as being "on", "over", "disposed on", "disposed over", "deposited on", or "deposited over" another element, it can be "directly on" the other element or intervening elements may also be present. In contrast, when an element is referred to as being "directly on", "directly over", or "disposed proximately to" another element, there are no intervening elements present.

Hereinbelow, exemplary embodiments of the present invention will be described in detail with reference to the accompanying drawings.

The present invention provides a method for preparing lactide comprising introducing an aqueous solution comprising lactic acid into a reactor filled with a catalyst and reacting the same to produce crude lactide vapor; and purifying the crude lactide vapor to produce lactide crystals (first purification step), wherein the first purification comprises collecting and crystallizing the crude lactide vapor using a first solvent to produce lactide crystals, and separating the lactide crystals from a residue through filtration.

Hereinbelow, each step of the lactide preparation method will be described in detail.

First, an aqueous solution comprising lactic acid is introduced into a reactor filled with a catalyst and reacted to produce crude lactide vapor.

This step prepares lactide from an aqueous solution comprising lactic acid using a solid oxide catalyst without going through a prepolymer. Preferably, the catalyst may be a solid catalyst containing tin selected from the group consisting of tin(IV) oxide and mixed or complex oxide thereof containing the oxidized state of (IV) of tin, and the solid catalyst may comprise an oxide of at least one metal selected from the group consisting of Si, Ti, Al, Zn, Zr, V, Cr, Mn, Fe, and Mo. In the case of using a nanocomposite oxide comprising tin(IV) oxide as a main component as a catalyst, the lactide production yield can be as high as 95% or higher.

A flow rate of the aqueous solution comprising lactic acid may be 0.1 kg/h to 3 kg/h per 1 kg of catalyst.

When the flow rate of the aqueous solution comprising lactic acid is less than 0.1 kg/h per 1 kg of catalyst, there may be a problem with respect to lactide productivity. In contrast, when said flow rate is greater than 3 kg/h per 1 kg of catalyst, a conversion rate of lactic acid may be low, leading to an increase in the cost of separation after the reaction.

The aqueous solution comprising lactic acid introduced into the reactor may be in a gaseous form. Preferably, the aqueous solution of lactic acid may be preheated and then provided in a gaseous form.

In the present step, for a smooth supply of the aqueous solution of lactic acid, it is preferable to introduce an inactive gas such as nitrogen, argon, or helium along with the aqueous solution of lactic acid. Further, said inactive gas quickly may remove byproducts such as lactide produced after reacting lactic acid, unreacted lactic acid, and water, thereby helping prevent an inactivation of the catalyst used for the lactic acid conversion.

Meanwhile, the flow rate of an inactive gas introduced with an aqueous solution of lactic acid may be 10 L/min to 300 L/min per 1 kg/h of the lactic acid flow rate. Herein, the flow rate of the inactive gas may be relative to 100% of lactic acid.

A higher flow rate of the inactive gas introduced into the reactor with the aqueous solution of lactic acid is more favorable in supplying lactic acid and removing byproducts such as lactide produced therefrom, unreacted lactic acid, and water. However, in the case where the flow rate exceeds 300 L/min per 1 kg/h of the lactic acid flow rate, the cost of gas introduction may increase.

between 0 and 0.1 at a temperature between 5° C. and 20° C., and the vapor pressure thereof is preferably between 5 hPa and 70 hPa at 20° C.

Additionally, according to Table 1 below, in which the solubilities of lactide according to different solvents are compared, a solvent which has a low solubility and high vapor pressure in lactide and is at least one selected from the group consisting of ethanol, propanol, and butanol is preferably used, but is not limited thereto, and any solvent can be used as long as it can be commonly used in the technical field to which the invention pertains. When a solvent with a high solubility such as methanol or ethyl acetate is used, the recovery rate of lactide crystal may be low during the collecting process of the lactide vapor. In contrast, when a solvent with a low vapor pressure is used, removing solutes adhered to the lactide crystals may be difficult. In particular, ethanol is the most preferable as it satisfies the above characteristics and is easily obtained from biomass.

TABLE 1

| Temperature (° C.) | Ethanol (EtOH) | Methanol (MeOH) | Ethyl acetate | 1-Propanol | 1-Butanol | Methylethyl ketone (MEK) |
|---|---|---|---|---|---|---|
| 10 | 0.04742 | 0.09534 | 0.21765 | 0.02037 | 0.00938 | 0.42132 |
| 15 | 0.06038 | 0.13175 | 0.29812 | 0.02757 | 0.01875 | 0.4842 |
| 20 | 0.072 | 0.15841 | 0.34526 | 0.03086 | 0.0275 | 0.57478 |
| 30 | 0.11849 | 0.24728 | 0.49944 | 0.04422 | 0.04094 | 0.77272 |
| 40 | 0.22231 | 0.47839 | 0.66593 | 0.09997 | 0.0797 | 1.01922 |
| 50 | 0.46749 | 1.2223 | 1.02007 | 0.27338 | 0.15408 | 1.63705 |
| 60 | 1.5481 | 3.13277 | 1.8 | 1.06736 | 0.52104 | 2.36797 |

Additionally, for a smooth supply of the aqueous solution of lactic acid, a dispersion plate can be used, which may decrease the flow rate of the inactive gases necessary for introduction with the aqueous solution of lactic acid.

In the present step, the reaction temperature for lactide vapor production by introducing and reacting the aqueous solution of lactic acid and the inactive gases into the reactor may be 170° C. to 250° C.

If the reaction temperature is between the range above, the conversion of lactic acid into lactide may be fast while preventing the production of oligomers from lactic acid polymerization.

In the present step, lactide can be produced under atmospheric pressure. Compared to the conventional preparation method for lactide by polymerization/depolymerization of lactic acid which requires high vacuum, the preparation method of the present invention is advantageous in terms of the operation of the process. However, for easier collection of lactide produced after the reaction and unreacted lactic acid, the reaction can be performed under a vacuum condition.

In the present step, other than the crude lactide vapor produced, byproducts such as unreacted lactic acid and water are generated. As lactide easily reacts with water and lactic acid and is denatured to a lactic acid dimer or trimer, a rapid separation of lactide which is produced after catalytic reaction from water and lactic acid may be necessary.

Second, a first purification step in which the crude lactide vapor is purified to produce a lactide crystal is carried out.

The first purification step may comprise collecting and crystallizing the crude lactide vapor using the first solvent to produce lactide crystals and separating the lactide crystals from a residue through filtration.

In the present step, the solubility of lactide in the first solvent used to collect the crude lactide vapor is preferably Additionally, in the present step, as the crude lactide vapor is crystallized in the first solvent, a residue may be separated from the lactide crystals through filtration. The residue comprises water, lactic acid, and the first solvent, which are the byproducts of the catalytic reaction. Through the present procedure, the lactide crystals may minimize contact between water and lactic acid, thereby increasing the recovery rate of lactide. In the present step, a conventional filtration technique may be used. Meanwhile, the first solvent needed for the present step may be used in combination with the cooled second solvent generated in the recrystallization step, which will be described hereinbelow, and may be supplied as much as it is removed through filtration as needed.

In the present step, the temperature of the first solvent to collect and crystallize the lactide vapor is preferably between 5° C. and 20° C. If the temperature is high, the solubility of lactide in the solvent may increase, leading to a decreased recovery rate of the lactide crystals. The temperature of the first solvent may be controlled in accordance with a type of the solvent to crystallize the crude lactide vapor. For example, using ethanol as the first solvent maintains the temperature at 20° C., thereby keeping the solubility of lactide in ethanol at 10 wt % or less. In the case where the first purification step is carried out, lactide crystals with an optical purity of 98% or higher can be recovered.

Additionally, after the first purification step, a second purification step of re-purifying the lactide crystal may be carried out.

The second purification may comprise dissolving the lactide crystals in the second solvent, which has the same components as the first solvent, recrystallizing the dissolved lactide crystals, and filtering and separating the recrystallized lactide crystals from the second solvent.

In the present step, the lactide crystals are dissolved and re-cooled to obtain the lactide crystals, and the impurities such as lactic acid which are not crystallized and water are dissolved in the second solvent to obtain lactide having a degree of polymerization equivalent to a PLA polymer. Additionally, in the present step, water and solvent adhered to the lactide crystals may be further removed through drying.

For example, in the present step, in the case of using ethanol as the second solvent, the weight ratio between ethanol and the lactide crystals in the dissolving step is preferably between 1:1 and 1:5. If the weight ratio is lower than 1:1, the lactide may have a lower purity. In contrast, if the weight ratio is higher than 1:5, as an amount of ethanol used increases, the reactor volume increases, and the recovery rate of the lactide crystals may decrease. The dissolution temperature in the dissolving step is preferably between 40° C. and 80° C. If the temperature is less than 40° C., the lactide crystals may be not fully dissolved in ethanol. In contrast, if the temperature is greater than 80° C., the lactide may react with the remaining water and lactic acid, and is hydrolyzed. The recrystallization temperature in the recrystallizing step is between −10° C. and 30° C. If the temperature is greater than 30° C., the recovery rate of lactide crystals may decrease and the lactic acid may have a high impurity content. In contrast, if the temperature is less than −10° C., an energy expenditure for cooling may be too high.

Additionally, the preparation cost may be reduced by re-supplying the second solvent separated in the second purification step as the first solvent in the first purification step. In the case where the second purification step is carried out, lactide crystals having an optical purity of 99% or higher may be recovered. Furthermore, for a higher optical purity, the second purification step may be repeated at least once.

Additionally, the preparation method of the present invention may further comprise distilling the residue separated in the first purification step to obtain the first solvent between the first and second purification steps, and introducing the obtained first solvent as the second solvent of the second purification step. Said distillation step may be to separate the first solvent from the residue comprising the lactic acid, water, and the first solvent separated in the first purification step. For the separation of the first solvent, a conventional distillation method may be used, and the separated first solvent may be used in the second purification step, and the rest of the lactic acid and water may be mixed with lactic acid raw materials and then reused. As the dissolution temperature of the solvent obtained in the above step through distillation is 70° C. or higher under atmospheric pressure, said solvent may be used for dissolving the lactide crystals in the second purification step.

Additionally, the present invention provides a lactide crystal, which is purified with an optical purity of 98% or higher according to the preparation method of the present invention.

The provided FIGURE shows a schematic diagram of the apparatus for preparation of lactide according to an embodiment of the present invention. With reference to this FIGURE, the apparatus for preparation of lactide of the present invention will be described.

The present invention provides an apparatus for preparing lactide comprising a catalytic reaction unit (10) filled with a solid catalyst (11) into which an aqueous solution comprising lactic acid is introduced to produce crude lactide vapor; a condensing unit (20) filled with a first solvent into which the crude lactide vapor produced in the catalytic reaction unit (10) is introduced to collect and crystallize the crude lactide vapor, thereby producing lactide crystals (21); and a first filtration unit (30), into which the lactide crystals (21) produced in the condensing unit (20) and a residue are introduced to separate the lactide crystals (21) by filtration.

A flow rate of the introduction of the aqueous solution comprising lactic acid into the catalytic reaction unit may be 0.1 kg/h to 3 kg/h per 1 kg of catalyst.

If the flow rate of the aqueous solution comprising lactic acid is less than 0.1 kg/h per 1 kg of catalyst, there may be a problem with respect to lactide productivity. In contrast, if said flow rate is greater than 3 kg/h, the recovery rate of lactic acid is low, leading to an increase in the cost of separation after the reaction increases.

When the crude lactide vapor is produced, the reactor temperature is between 170° C. and 250° C. If the reactor temperature is less than 170° C., the crude lactide vapor may be not easily produced. In contrast, if the reactor temperature is greater than 250° C., an oligomer may be produced by polymerization of lactic acid.

When the crude lactide vapor is introduced into the catalytic reaction unit, the reaction pressure may be atmospheric pressure. Producing lactide by a conventional polymerization/depolymerization of lactic acid has an advantage in terms of the operation of the process, compared to a production in which high vacuum is needed. However, for easy recovery of lactide produced after the reaction and unreacted lactic acid, the reaction may be carried out under high vacuum.

The lactide crystals in the condensing unit (20) may be dispersed in the first solvent.

The condensing unit (20), to which the first filtration unit (30) is linked, may fill the first solvent, crystallize the crude lactide vapor in the first solvent, and separate the aqueous solution of lactic acid and uncrystallized lactide through the first filtration unit, but is not limited thereto.

The first filtration unit (30) is not particularly limited, and may be a filtration unit which is conventionally used in the art.

The aqueous solution of lactic acid is supplied in a raw material supplying unit (70), purified and condensed in a water separating unit (80), and then introduced into the catalytic reaction unit (10). The aqueous solution of lactic acid passes through the catalytic reaction unit (10) along with a carrier gas such as nitrogen, and accordingly, the lactide produced after the catalytic reaction is maintained in a vapor form along with water, unreacted lactic acid, the carrier gas, and byproducts thereof. The carrier gas may pass through the condensing unit (20) and the first filtration unit (30), and then be reused and introduced into the catalytic reaction unit (10).

The water separating unit (80) may use a conventional distillation system for water vaporization. To prevent dimerization of lactic acid, water distillation is preferably performed at a temperature of 80° C. or lower.

Preferably, the apparatus of the present invention may further comprise a first recrystallization unit (40), into which the lactide crystals (21) obtained by the first filtration unit (30) and the second solvent which has the same components as the first solvent are introduced and in which the lactide crystals (21) are dissolved and recrystallized by the second solvent; and a second filtration unit (50) in which the recrystallized lactide crystals (41) and the second solvent are introduced to separate the recrystallized lactide crystals (41) through filtration.

Preferably, the apparatus of the present invention may further comprise a distillation unit (60), in which the residue separated by the first filtration unit (30) is introduced and distilled to obtain the first solvent, wherein the distillation unit (60) supplies the first solvent obtained by the distillation unit (60) to the first recrystallization unit (40) as the second solvent. The remaining lactic acid and water in the distillation unit (60) may be supplied to the raw material supplying unit (70) to be used for lactide production.

Preferably, the second filtration unit (50) may further carry out a function of re-supplying the second solvent separated in the second filtration unit (50) to the condensing unit (20) as the first solvent.

Preferably, the apparatus of the present invention may further comprise a second recrystallization unit, which has the same function as the first recrystallization unit (40) and into which the recrystallized lactide crystals (41) separated in the second filtration unit (50) are introduced, and a third filtration unit. The second recrystallization unit and the third filtration unit may be for repeating the second purification step at least once for a higher optical purity, which may be carried out in the first recrystallization unit (40) and the second filtration unit (50) without an additional apparatus.

Hereinbelow, Examples and Comparative Examples of the present invention are described.

Preparation Example 1: Preparation of $SnO_2(80)/SiO_2$ Catalyst 37 g of $SnCl_4 \cdot 5H_2O$ and 13.75 g of silica sol (Ludox, SM30) were added to a beaker maintained at 5° C. and stirred, and the pH was adjusted to 8 with 0.2 M NaOH. The temperature was then raised to 70° C., and the mixture was stirred for an additional four hours. A precipitate produced therefrom was dried for five hours at 100° C., and was finally calcinated for two hours at 450° C. to obtain a catalyst comprising 80 wt % of tin oxide and 20 wt % of silica. As a result of X-ray diffraction analysis of the obtained catalyst, peaks related to a tin compound was identified as $SnO_2$ phases. Accordingly, the catalyst synthesized by the above synthesis method is abbreviated as $SnO_2$ (80 wt %, hereinafter, units are omitted)/$SiO_2$ catalyst.

Example 1: Preparation of Lactide Using $SnO_2(80)/SiO_2$ Catalyst and Recovery of Lactide Using Ethanol as Solvent 1 g of $SnO_2(80)/SiO_2$ was filled into a fixed bed reactor, and the temperature of the reactor was maintained at 240° C. under atmospheric pressure. Then, a 75 wt % aqueous solution of L-lactic acid (Aldrich) was introduced into the catalytic reactor at a flow rate of 1.0 g/h after mixing nitrogen gas. Meanwhile, the vapor produced after the catalytic reaction was collected using a condenser filled with 35 g of ethanol. The condenser was maintained at 5° C.

After continuing the reaction for 100 hours under the above condition, 75.1 g of solid crystals were extracted from the condenser through filtration and drying. Gas chromatography analysis and Karl Fischer analysis of the solid crystals showed 98.5 wt % L-lactide, 0.5 wt % meso-lactide, and 1.0 wt % water.

The result shows that by producing lactide using a $SnO_2$ (80)/$SiO_2$ catalyst and using ethanol as a solvent for collecting lactide vapor, L-lactide may be produced and collected from L-lactic acid with a high production yield of 90% or higher.

Example 2: Preparation of Lactide Using $SnO_2(80)/SiO_2$ Catalyst and Recovery of Lactide Using 1-Propanol as Solvent The same method as Example 1 was used to produce and recover lactide, except that 1-propanol was filled into the condenser instead of ethanol.

After continuing the reaction for 100 hours under the above condition, 76.5 g of solid crystals were extracted in the condenser through filtration and drying. Gas chromatography analysis and Karl Fischer analysis of the solid crystals showed 99.0 wt % L-lactide, 0.5 wt % meso-lactide, and 0.5 wt % water.

The result shows that by producing lactide using a $SnO_2$ (80)/$SiO_2$ catalyst and using 1-propanol as a solvent for collecting lactide vapor, L-lactide may be produced and collected from L-lactic acid with a high production yield of 92% or higher.

Example 3: Preparation of Lactide Using $SnO_2(80)/SiO_2$ Catalyst and Recovery of Lactide Using 1-Butanol as Solvent The same method as Example 1 was used to produce and recover lactide, except that 1-butanol was filled into the condenser instead of ethanol.

After continuing the reaction for 100 hours under the above condition, 58.1 g of solid crystals were extracted in the condenser through filtration and drying. Gas chromatography analysis and Karl Fischer analysis of the solid crystals showed 98.0 wt % L-lactide, 0.5 wt % meso-lactide, and 1.5 wt % water.

The result shows that by producing lactide using a $SnO_2$ (80)/$SiO_2$ catalyst and using 1-butanol as a solvent for collecting lactide vapor, L-lactide may be produced and collected from L-lactic acid with a high production yield of 70% or higher.

Example 4: Recovery of Lactide According to Recrystallization Steps Using Ethanol as Solvent 10 g of lactide crystals prepared in Example 1 were mixed with 30 g of ethanol was heated to 50° C., and then stirred for 30 minutes to dissolve the lactide crystals. Then, the ethanol in which the lactide had been dissolved was cooled to 20° C. and maintained for 1 hour to extract the lactide crystals.

A weight of the obtained solid crystal after being separated through filtration/drying was 8.5 g, and gas chromatography analysis and Karl Fischer analysis of the solid crystals showed more than 99.9% L-lactide, and no water was found.

Comparative Example 1: Preparation of Lactide Using $SnO_2(80)/SiO_2$ and Recovery of Lactide Using γ-Butyrolactone as Solvent The same method as Example 1 was used to produce and recover lactide, except that γ-butyrolactone was filled into the condenser instead of ethanol.

After continuing the reaction for 100 hours under the above condition, no solid crystal was formed and such result shows that using γ-butyrolactone having a high solubility in lactide does not result in recovery of lactide in a crystalline form.

The results are shown in Table 2 below.

TABLE 2

| Examples | L-lactide Content (%) | Meso-lactide Content (%) | Water Content (%) |
|---|---|---|---|
| Example 1 | 98.5 | 0.5 | 1.0 |
| Example 2 | 99.0 | 0.5 | 0.5 |

TABLE 2-continued

| Examples | L-lactide Content (%) | Meso-lactide Content (%) | Water Content (%) |
|---|---|---|---|
| Example 3 | 98.0 | 0.5 | 1.5 |
| Example 4 | 99.9 | — | — |
| Comparative Example 1 | — | — | — |

Based on the above description, one of ordinary skill in the art to which the present invention pertains will be able to understand that the present invention may be embodied in other specific forms without modifying the technical concepts or essential features of the present invention. In this regard, the above-described examples are for illustrative purposes only, and the invention is not intended to be limited by these examples. For example, each component described in a singular form may be embodied in a distributed form. Likewise, components described in a distributed form may be embodied in a combined form.

The present invention is intended to cover not only the exemplary embodiments but also various alternatives, modifications, equivalents, and other embodiments that may be included within the spirit and scope of the present invention as defined by the appended claims.

REFERENCE NUMERALS

10: Catalytic reaction unit
11: Solid catalyst
20: Condensing unit
21: Lactide crystals
30: First filtration unit
40: First recrystallization unit
41: Recrystallized lactide crystals
50: Second filtration unit
60: Distillation unit
70: Raw material supplying unit
80: Water separating unit

The invention claimed is:

1. A method for preparing lactide comprising:
(i) introducing an aqueous solution comprising lactic acid into a reactor filled with a catalyst and reacting the same to produce crude lactide vapor comprising lactide, lactic acid, and water; and
(ii) purifying the crude lactide vapor produced in the step (i) to produce lactide crystals, wherein the step (ii) comprises:
(ii-a) cooling, collecting and crystallizing the crude lactide vapor at a temperature between 5° C. and 20° C. in a condenser containing ethanol or propanol as a first solvent to produce lactide crystals, and
(ii-b) separating the lactide crystals from a residue through filtration.

2. The method of claim 1, wherein the steps (ii-a) and (ii-b) are conducted simultaneously.

3. The method of claim 1, further comprising (iii) re-purifying the lactide crystals after the step (ii),
wherein the step (iii) comprises:
(iii-a) dissolving the lactide crystals in a second solvent which has the same components as the first solvent, wherein the solvent is ethanol or propanol,
(iii-b) recrystallizing the dissolved lactide crystals, and
(iii-c) filtering and separating the recrystallized lactide crystals from the second solvent.

4. The method of claim 3, wherein the weight ratio between the second solvent in the step (iii-a) and the lactide crystals is between 1:1 and 1:5.

5. The method of claim 3, wherein the dissolution temperature of the step (iii-a) is between 40° C. and 80° C.

6. The method of claim 3, wherein the recrystallization temperature of the step (iii-b) is between −10° C. and 30° C.

7. The method of claim 3, further comprising re-supplying the second solvent separated in the step (iii-c) as the first solvent of the step (ii) after the step (iii).

8. The method of claim 3, further comprising distilling the residue separated in step (ii) between the steps (ii) and (iii) to obtain the first solvent, and introducing the obtained first solvent as the second solvent of the step (iii).

9. The method of claim 1, wherein the catalyst is a tin-containing solid catalyst comprising a tin(IV) oxide or a mixed or complex oxide thereof containing the oxidized state (IV) of tin.

10. The method of claim 9, wherein the solid catalyst comprises an oxide of at least one metal selected from the group consisting of Si, Ti, Al, Zn, Zr, V, Cr, Mn, Fe, and Mo.

11. An apparatus for preparing lactide comprising:
a catalytic reaction unit filled with a solid catalyst into which an aqueous solution comprising lactic acid is introduced to produce crude lactide vapor comprising lactide, lactic acid, and water;
a condensing unit filled with ethanol or propanol as a first solvent into which the crude lactide vapor produced in the catalytic reaction unit is introduced to cool, collect and crystallize; and
a first filtration unit, into which the lactide crystals produced in the condensing unit and a residue are introduced to separate the lactide crystals by filtration.

12. The apparatus of claim 11, further comprising:
a first recrystallization unit into which the lactide crystals obtained by the first filtration unit and a second solvent which is ethanol or propanol are introduced and in which the lactide crystals are dissolved and recrystallized by the second solvent; and
a second filtration unit into which the recrystallized lactide crystals and the second solvent are introduced to separate the recrystallized lactide by filtration.

13. The apparatus of claim 12, further comprising a distillation unit in which the residue separated by the first filtration unit is introduced and distilled to obtain the first solvent, wherein the distillation unit supplies the first solvent obtained by the distillation unit to the first recrystallization unit as the second solvent.

14. The apparatus of claim 12, the second filtration unit further carries out a function of re-supplying the second solvent separated in the second filtration unit to the condensing unit as the first solvent.

15. The apparatus of claim 12, further comprising a second recrystallization unit, which carries out the same function as the first recrystallization unit and into which the recrystallized lactide crystals separated in the second filtration unit are introduced, and a third filtration unit.

* * * * *

UNITED STATES PATENT AND TRADEMARK OFFICE
CERTIFICATE OF CORRECTION

PATENT NO. : 10,253,012 B2
APPLICATION NO. : 15/290647
DATED : April 9, 2019
INVENTOR(S) : Dong Won Hwang et al.

Page 1 of 1

It is certified that error appears in the above-identified patent and that said Letters Patent is hereby corrected as shown below:

In the Claims

Column 14, Line 33, insert the following after the word "crystallize" and before ";":
-- the crude lactide vapor at a temperature between 5°C. and 20°C., thereby producing lactide crystals --

Signed and Sealed this
Sixteenth Day of February, 2021

Drew Hirshfeld
*Performing the Functions and Duties of the
Under Secretary of Commerce for Intellectual Property and
Director of the United States Patent and Trademark Office*